United States Patent [19]

Ravi et al.

[11] Patent Number: 4,959,468

[45] Date of Patent: Sep. 25, 1990

[54] COLOR STABILIZATION METHOD FOR GLYCOSIDE PRODUCTS

[75] Inventors: Prasad S. Ravi, Decatur; Hunter L. Kickle, Mt. Zion; Patrick M. McCurry, Decatur; David J. Skogberg, Decatur, all of Ill.

[73] Assignee: Henkel Kommanditgesellschaft auf Aktien, Duesseldorf, Fed. Rep. of Germany

[21] Appl. No.: 333,820

[22] Filed: Apr. 3, 1989

Related U.S. Application Data

[63] Continuation of Ser. No. 61,859, Jun. 12, 1987, abandoned.

[51] Int. Cl.$^5$ ............................................. C07H 1/06
[52] U.S. Cl. ....................... 536/127; 536/4.1; 536/18.5; 536/18.6; 536/124; 127/46.1
[58] Field of Search ............... 536/4.1, 18.5, 18.6, 536/124, 127; 127/46.1

[56] References Cited

U.S. PATENT DOCUMENTS

| | | | |
|---|---|---|---|
| 2,235,783 | 3/1941 | White | 536/4.1 |
| 2,356,565 | 8/1944 | Chwala | 536/4.1 |
| 2,390,507 | 12/1945 | Cantor | 536/4.1 |
| 2,422,328 | 6/1947 | Young | 106/126 |
| 2,867,651 | 1/1959 | Wise | 560/98 |
| 3,219,656 | 11/1965 | Boettner | 536/4.1 |
| 3,221,031 | 11/1965 | Huffman | 549/205 |
| 3,375,243 | 3/1968 | Nevin et al. | 536/4.1 |
| 3,450,690 | 6/1969 | Gibbons et al. | 536/4.1 |
| 3,547,828 | 12/1970 | Mansfield et al. | 252/351 |
| 3,598,865 | 8/1971 | Lew | 536/4.1 |
| 3,640,998 | 2/1972 | Mansfield et al. | 536/4.1 |
| 3,687,999 | 8/1972 | Kapur et al. | 558/21 |
| 3,707,535 | 12/1972 | Lew | 536/4.1 |
| 3,721,633 | 3/1973 | Ranauto | 252/527 |
| 3,737,426 | 6/1973 | Throckmorton et al. | 536/4.1 |
| 3,772,269 | 11/1973 | Lew | 536/4.1 |
| 3,829,318 | 10/1974 | Mansfield | 536/4.1 |
| 3,865,880 | 2/1975 | Quelly et al. | 568/410 |
| 3,974,138 | 8/1976 | Lew | 536/18.6 |
| 4,011,389 | 3/1977 | Langdon | 536/18.6 |
| 4,223,129 | 9/1980 | Roth et al. | 536/18.6 |
| 4,472,170 | 9/1984 | Hellyer | 44/51 |
| 4,507,472 | 3/1985 | Usher et al. | 536/51 |
| 4,557,729 | 12/1985 | McDaniel et al. | 8/111 |
| 4,704,453 | 11/1987 | Lorenz et al. | 536/124 |
| 4,762,918 | 8/1988 | McDaniel, Jr. et al. | 536/124 |

FOREIGN PATENT DOCUMENTS

| | | | |
|---|---|---|---|
| 3232791 | 3/1984 | Fed. Rep. of Germany | 536/18.5 |
| 802860 | 10/1958 | United Kingdom . | |
| 981965 | 2/1965 | United Kingdom . | |

OTHER PUBLICATIONS

Article entitled, "Eliminating Color, Odor Problems with Sodium Borohydride", from the Jun. 1978 Soap/Cosmetics/Chemical Specialties, by Herman.

*Primary Examiner*—Ronald W. Griffin
*Assistant Examiner*—Nancy S. Carson
*Attorney, Agent, or Firm*—Ernest G. Szoke; Wayne C. Jaeschke; Daniel S. Ortiz

[57] ABSTRACT

Glycoside products having a propensity to discolor (i.e., darken) under aqueous alkaline conditions are stabilized against discoloration under such conditions by treatment with from about 0.01 to about 2 weight percent (glycoside product dry weight basis) of a borohydride material such as sodium borohydride, potassium borohydride, lithium borohydride, etc.

17 Claims, No Drawings

COLOR STABILIZATION METHOD FOR GLYCOSIDE PRODUCTS

This application is a continuation of application Ser. No. 061,859, filed 6/12/87, now abandoned.

BACKGROUND OF THE INVENTION

This invention pertains generally to the manufacture and/or treatment of glycoside products and, in particular, to a method of imparting to such products resistance to discoloration (i.e., darkening) upon exposure (especially prolonged exposure such as from 3 to 6 months or more) to elevated temperatures (e.g., in excess of about 40° C.) and/or upon exposure to alkaline conditions (e.g., at pH's in excess of about 7). Briefly stated, the indicated method entails treating the discoloration-prone (or color-unstable) glycoside product of concern with a relatively small, but effective amount of a borohydride material.

Glycoside materials such as lower alkyl (e.g., methyl, ethyl, propyl, butyl, etc.) glycosides; higher alkyl (e.g., $C_6$–$C_{30}$ alkyl) glycosides; and the like are known items which are suitable for use in a wide variety of applications ranging from usage as a reactive polyol in the preparation of condensation polymer products such as urethane polymers and polyester resins to utilization as a surface active agent in detergent compositions and other cleansing products, in agricultural treatment compositions, and the like.

Generally speaking, alkyl glycosides are conveniently prepared by reacting an alcohol of the type and chain length which is desired to form the "alkyl" portion of the glycoside of interest with a saccharide reactant (e.g., a monosacchraride such as glucose, xylose, arabinose, galactose, fructose, etc., or a polysaccharide such as starch, hemicellulose, lactose, maltose, melibiose, etc.) or with a glycoside starting material wherein the aglycone portion thereof is different from the alkyl substituent desired for the ultimate alkyl glycoside product of interest. Typically, such reaction is conducted at an elevated temperature and in the presence of an acid catalyst. Various alkyl glycoside products and processes for making same are disclosed in U.S. Pat. No. 2,235,783 (White, issued Mar. 18, 1941); U.S. Pat. No. 2,356,565 (Chwala, issued Aug. 22, 1944); U.S. Pat. No. 2,390,507 (Cantor, issued Dec. 11, 1945); U.S. Pat. No. 2,442,328 (Young, issued Jun. 17, 1947); U.S. Pat. No. 3,219,656 (Boettner, issued Nov. 23, 1965); U.S. Pat. No. 3,375,243 (Nevin et al., issued Mar. 26, 1968); U.S. Pat. No. 3,450,690 (Gibbons et al., issued Jun. 17, 1969); U.S. Pat. No. 3,547,828 (Mansfield et al., issued Dec. 15, 1970) U.S. Pat. No. 3,598,865 (Lew, issued Aug. 10, 1971); U.S. Pat. No. 3,640,998 (Mansfield et al., issued Feb. 8, 1972); U.S. Pat. No. 3,707,535 (Lew, issued Dec. 26, 1972); U.S. Pat. No. 3,721,633 (Ranauto, issued Mar. 20, 1973); U.S. Pat. No. 3,737,426 (Throckmorton et al., issued Jun. 5, 1973); U.S. Pat. No. 3,772,269 (Lew, issued Nov. 13, 1973); U.S. Pat. No. 3,839,318 (Mansfield, issued Oct. 1, 1974); U.S. Pat. No. 3,974,138 (Lew, issued Aug. 10, 1976); U.S. Pat. No. 4,011,389 (Langdon, issued Mar. 8, 1977); and U.S. Pat. No. 4,223,129 (Roth et al., issued Sept. 16, 1980).

In the preparation of alkyl glycoside products, it is not uncommon for such products to develop an undesirably dark coloration during the course of the synthesis and isolation procedures employed. Various procedures have been suggested for improving the color of such dark colored glycoside products including, for example, treatment with bleaching reagents such as hydrogen peroxide; intentional color formation by heat treatment under alkaline conditions followed by removal (e.g., by precipitation, filtration, etc.) of dark colored impurities generated during said treatment procedure; treatment with decolorizing adsorbents such as particulate carbon materials, etc.; and the like. See in this regard, for example, Gibbons' U.S. Pat. No. 3,450,690 which discloses an alkaline heat treatment/separation procedure that can optionally be followed by treatment with bleaching agents such as hydrogen peroxide or by treatment with decolorizing carbons. See also Cantor's U.S. Pat. No. 2,390,507; White's U.S. Pat. No. 2,235,783; Example 1 of Throckmorton et al.'s U.S. Pat. No. 3,737,426; Examples 5 and 10 of Langdon's U.S. Pat. No. 4,011,389; and Example 1 of U.S. Pat. No. 4,472,170 to Hellyer (issued Sept. 18, 1984) for teachings related to the use of carbon adsorbents for the decolorization of various alkyl glycoside products.

Even when glycoside products are originally prepared (or are subsequently decolorized in accordance with one or more of the procedures set forth above) in a fashion which results in initial color characteristics acceptable for certain applications, such products nonetheless commonly exhibit a propensity to discolor (i.e., darken) as a function of time even under relatively mild storage conditions (e.g., at neutral or slightly acidic pH and normal room temperatures, i.e., 20°–25° C.). The propensity to discolor is greatly accentuated (i.e., in terms of the intensity and rapidity thereof) by exposure to elevated temperatures (such as, for example, in the range of 40° to 100° C. or more) and/or exposure to relatively strong alkaline aqueous environments (i.e., pH of 8 to 12). Generally speaking, the extent of discoloration is related to the severity of the pH/temperature/time to which the glycoside product is exposed.

In U.S. Pat. No. 4,557,729 to McDaniel et al. (issued Dec. 10, 1985), the aforementioned problem of color deterioration of glycoside products during storage thereof is discussed and a method for obviating such problem is disclosed which entails first bleaching the glycoside product of interest with an oxidizing agent such as ozone, hydrogen peroxide, hypochlorite salts, etc., and thereafter exposing the resulting bleached glycoside product to a source of sulfur dioxide (e.g., sulfur dioxide gas, sodium sulfite, sodium metabisulfite, sodium hydrosulfite, etc.) to stabilize said glycoside product against color degradation. While the indicated method has been found to be quite effective in stabilizing the color of glycoside products against deterioration or darkening thereof under relatively mild storage conditions (e.g., at pH's in the range of from about 3 to about 7 and at temperatures in the range of from about 20° to about 30° C.), it has also been found to be not nearly as effective (and, in fact, less effective than is desired in many cases) in stabilizing against color deterioration under harsher conditions such as those involving prolonged storage at elevated temperatures (e.g., 35° to 60° C. or more) and those involving relatively high pH (e.g., pH=8 or more) environments, even in situations involving relatively short term/low temperature exposure. Accordingly, it would be highly desirable to provide a method for imparting improved high temperature and/or alkaline color stability to glycoside products which are otherwise prone to darken substantially upon exposure to high temperatures and/or alkaline conditions.

SUMMARY OF THE INVENTION

It has now been discovered that glycoside products having a propensity to discolor (i.e., darken) under aqueous alkaline conditions and/or upon prolonged exposure to elevated temperatures can be stabilized to substantially reduce the degree or extent of discoloration thereof under such conditions by treatment with a small but effective amount of a borohydride material. In accordance with the foregoing, the present invention in one of its main aspects is a method for improving the color stability of glycoside products, said method comprising the step of treating said glycoside product with from about 0.01 to about 2 weight percent, on a glycoside product dry weight basis, of a borohydride material.

In another of its aspects, the present invention involves a multistep process wherein the glycoside starting material is an undesirably dark glycoside product at the outset and wherein said product is subjected to an oxidative bleaching operation to substantially improve (i.e., lighten) the color thereof prior to the above-described borohydride treatment.

In yet another aspect, which is particularly useful and significant in the case of extremely dark colored glycoside starting materials, the present invention is embodied in a multistep process in which said glycoside product is initially decolorized by treatment with a porous, particulate carbon adsorbent; the carbon adsorbent is then removed from the glycoside product (e.g., by filtration, centrifugation, etc.); and the resulting carbon-treated glycoside product is subsequently subjected to the above-described borohydride treatment. Within this latter embodiment, it is oftentimes beneficial and preferred to include an oxidative bleaching step or operation of the type referred to above following the indicated carbon treatment and removal steps and prior to the borohydride treatment operation hereof.

In ascertaining and/or quantifying the color characteristics (e.g., the relative darkness or lightness) of glycoside products for the purpose of the present invention, it is convenient to utilize the extinction coefficient of the glycoside material of interest (e.g., before treatment, after treatment, before and after exposure to elevated temperatures and/or to alkaline conditions, etc.) at a glycoside concentration of 10–50 weight percent in aqueous solution using a suitable spectrophotometer (e.g., a Spectronic 20) over a path length of 1 cm and using 470 nm wavelength light. Since extinction coefficient is essentially a measure of the ability of the glycoside solution of concern to absorb light as opposed to transmitting same, relatively larger extinction coefficients correspond to relatively darker colored glycoside solutions. Accordingly, the methodology of the present invention has the effect of providing glycoside products which have lower extinction coefficients when determined by this test method following prolonged exposure to high temperatures or following short or long term exposure to alkaline conditions (at either high or low temperatures) than such products would otherwise exhibit without having been treated in accordance with the present invention.

The term "extinction coefficient" as used herein refers to the calculated absorbance of a theoretical solution containing one gram of solid material per cm$^3$ of solution measured as described above and calculated according to the following formula:

$$E_{470} = A/(c \text{ times } l)$$

wherein:
A = measured absorbence @470 nm
c = concentration in grams per cm$^3$
l = pathlength in centimeters and
$E_{470}$ = extinction coefficient at 470 nm.

DETAILED DESCRIPTION OF THE INVENTION

Glycoside products to which the present invention is beneficially applicable include any glycoside materials (e.g., long chain alkyl monoglycosides, long chain alkyl polyglycosides, short chain alkyl mono- and polyglycosides, etc.) which are prone to darken (or discolor) to a significant extent upon prolonged exposure to elevated temperatures and/or upon short or long term exposure (at either high or low temperatures or both) in alkaline (e.g., pH's above about 7) aqueous solutions.

Generally speaking, glycoside materials to which present invention is applicable include those of the formula:

$$RO(R'O)_y(Z)_x \qquad (A)$$

wherein R is a monovalent organic radical (e.g., a monovalent saturated aliphatic, unsaturated aliphatic or aromatic radical such as alkyl, hydroxyalkyl, alkenyl, hydroxyalkenyl, aryl, alkylaryl, hydroxyalkylaryl, arylalkyl, alkenylaryl, arylalkenyl, etc.) containing from as little as one up to about 30 carbon atoms (preferably from 1 to about 18 carbon atoms and more preferably from 1 to about 16 carbon atoms); R' is a divalent hydrocarbon radical containing from 2 to about 4 carbon atoms; y is a number having an average value of from 0 to about 12 (preferably from 0 to about 5 and most preferably 0); Z represents a moiety derived from a reducing saccharide containing 5 or 6 carbon atoms (most preferably arabinose, xylose, glucose, galactose and combinations thereof); and x is a number having an average value from 1 to about 6 (preferably from 1 to about 3 and most preferably from 1 to about 2).

Within the above-described group of glycoside materials are included relatively short chain (e.g., $C_1$ to about $C_6$, (preferably $C_1$ to about $C_4$) organo glycosides which generally find use as chemical intermediates and/or as reactive polyols for use in condensation polymerized (or polymerizable) systems or products (e.g., polyester resins, polyurethanes, etc.) in a variety of adhesive and coatings applications. Also included are relatively long chain (e.g., $C_6$ to about $C_{30}$, preferably $C_8$ to about $C_{18}$, and most preferably $C_8$ to about $C_{16}$) organo glycoside materials which are surface active in character and which are suitable for use as wetting agents, foaming agents, surfactants, etc. in a wide variety of end use applications.

Glycoside products suitable for treatment in accordance with the present invention also include derivatives of products of the formula A above including, for example, those in which one or more of the normally free (i.e., unreacted) hydroxyl groups of the saccharide moiety, Z, have been alkoxylated (preferably, ethoxylated or propoxylated) so as to attach one or more pendant alkoxy or poly (alkoxy) groups in place thereof. In the case of the indicated alkoxylated derivatives, the amount of alkylene oxide (e.g., ethylene oxide, propylene oxide, etc.) employed will generally correspond to from about 1 to about 20 (preferably about 3 to about 10) moles thereof per mole of saccharide moiety.

In regard to the foregoing, it should be noted that pure glycoside products of the formula A above are, generally speaking, color-free (or light in color) and are not prone to discoloration (i.e., darkening) upon exposure to aqueous alkaline conditions or to elevated temperatures. However, by-products which are apparently unavoidably generated to one degree or another during the acid-catalyzed alcohol/saccharide reaction employed to prepare such glycoside products are either dark in color as originally generated or latently prone to darkening upon subsequent exposure to elevated temperatures (e.g., during evaporative removal of excess, unreated alcohol from the reaction mixture) or to alkaline conditions or upon prolonged storage under even relatively mild (e.g., ambient room temperature and neutral pH) storage conditions. Moreover, even when dark colored reaction products are subjected to oxidative bleaching operations to lighten the color thereof to acceptable levels, the resulting bleached reaction products have been found to still contain materials (e.g., either as residual color-forming species which survive the bleaching operation and/or as color-forming species generated during said bleaching operation) which are prone to darken substantially (and to an unacceptable degree) upon prolonged storage at elevated temperatures and/or upon exposure to alkaline conditions. Further, such propensity to darken substantially under the indicated conditions has been found to persist even after post-bleaching sulfur dioxide treatment of the resulting reaction product in accordance with McDaniel et al.'s U.S. Pat. No. 4,557,729.

In practicing the process or method of the present invention, the discoloration-prone glycoside product of interest is contacted with a relatively small but effective amount of a borohydride material for a time sufficient to substantially reduce the propensity of said glycoside product to darken upon exposure to elevated temperatures and/or alkaline conditions.

Suitable borohydride materials for use in said method include Group I and Group II metal borohydride salts such as alkali metal borohydride salts, alkaline earth metal borohydride salts, zinc borohydride, etc. as well as substituted derivatives of such borohydride salts such as, for example, alkali metal cyanoborohydrides, alkylated or alkoxylated borohydride salts, quaternary ammonium borohydride salts, strong base resins in the borohydride salt form, and the like. Preferred for use are the alkali metal borohydride salts, especially sodium borohydride, lithium borohydride and potassium borohydride.

The amount of borohydride material used in the indicated treatment will depend largely upon the severity or intensity of the discoloration propensity characteristics of the glycoside product to be treated and upon the particular conditions (e.g., treatment temperature, treatment time, etc.) chosen under which to conduct said treatment. As a general rule, however, the borohydride material is employed in an amount ranging from about 0.01 to about 2 (preferably from about 0.01 to about 1 and most preferably from about 0.05 to about 0.4) weight percent on a glycoside product dry weight basis.

Typically, the indicated borohydride treatment is conducted at a temperature of from about 20 to about 75 (preferably from about 30° to about 60° and most preferably from about 40° to about 50°) C. and for a treatment time period of from about 1 to about 100 (preferably from about 4 to about 50 and most preferably from about 8 to about 24) hours. As a general rule for a given discoloration-prone glycoside feedstock, operation toward the higher end of the indicated temperature ranges permits the use of relatively shorter treatment times but may require the use of somewhat larger amounts of borohydride material.

Generally speaking, the pressure at which the borohydride treatment is conducted can be, as may be desired in a given instance, atmospheric, subatmospheric or superatmospheric.

Typically the indicated borohydride treatment is conducted in the context of a liquid phase which can, depending upon the circumstances and the particular glycoside product involved, take the form of (a) an aqueous solution of said glycoside product; (b) a solution of said glycoside product in an organic liquid in which it is soluble (e.g., residual or excess alcohol reactant, etc.); or (c) a melt of the glycoside product to be treated. Naturally, when the treatment is conducted under non-aqueous conditions (e.g., in a glycoside melt or in organic glycoside solution) and the borohydride material is a metallic borohydride material, there are certain limits or constraints upon the solubility of said borohydride material in the non-aqueous treatment medium. In some such cases, the indicated solubility limit will be sufficiently high under the treatment conditions (e.g., temperature, etc.) of interest to accommodate (i.e., permit the dissolution of) the borohydride dosage desired for use in the treatment of concern. In other such cases, however, it may be desirable or necessary to employ a borohydride material having an organic substituent or cation or to use a compatibilizing solvent component and/or to employ a substantially increased treatment temperature to attain adequate solubilization and reaction of the desired borohydride dosage in the non-aqueous treatment medium of interest.

In those instances wherein the glycoside product is to be treated in non-aqueous form such as in melt form or in the form of a solution in an organic liquid in which said glycoside product is soluble (e.g., residual or excess alcohol reactant such as a fatty alcohol in the case of long chain organo glycoside products or a lower alkanol in the case of lower alkyl glycoside products), the glycoside product will typically constitute from about 10 to about 100 (preferably from about 20 to about 90 and most preferably from about 40 to about 70) weight percent of said solution on a total solution weight basis during said treatment. Advantageously, this particular type of treatment is conducted prior to or during (preferably prior to) the evaporative removal of excess alcohol reactant in the course of recovering the glycoside product of concern from the reaction mixture in which it was originally prepared.

In a particularly preferred embodiment, the color stabilization treatment hereof involves treating the discoloration-prone glycoside product of concern in the form of an aqueous solution thereof in which said glycoside product constitutes from about 10 to about 90 (preferably about 20 to about 80 and most preferably from about 40 to about 75) weight percent of said solution on a total solution weight basis. In connection with particular embodiment, the borohydride treatment is generally conducted within the time, temperature and borohydride concentration ranges which are set forth above and at an aqueous solution pH of at least about 8 (preferably in the range of from about 10 to about 13, most preferably from about 11 to about 12). In those instances wherein alkali metal cyanoborohydride salts are employed as the borohydride treatment material hereof, the borohydride treatment can advantageously be conducted under acidic pH conditions (e.g., at pH's as low as about 3 or less, for example) since those particular borohydride salts are relatively stable to decomposition under the indicated pH conditions. In some instances, it is advantageous to include from about 0.5 to about 20 weight percent (aqueous glycoside solution weight basis) of a lower alkanol (especially ethanol) in the aqueous glycoside solution during or following the borohydride treatment in order to reduce the viscosity of said solution and/or to control the foaming which may occur during said treatment.

Following completion of the above-described borohydride treatment step, all or most of the residual, unreacted borohydride material, if any, can (if desired) be destroyed, neutralized or quenched by either raising the temperature of the reaction mixture to a value in the range of from about 60° to about 80° C. or more and/or by neutralizing the borohydride with an acidic material. In the context of an aqueous treatment operation (and depending upon the treatment pH and borohydride material employed), this latter option may entail reducing the pH of the aqueous reaction mixture to a value of about 8 or less, however, in many cases reduction of the pH to a value in the range of about 9 to less than about 10 will be sufficient for the stated purpose.

As has been noted above, one embodiment of the present invention entails a multistep process wherein the glycoside product is initially decolorized by treatment thereof with a porous particulate carbon adsorbent; the glycoside product is then separated from the carbon adsorbent; and the carbon-treated glycoside product is subsequently subjected to the above-described borohydride treatment, either without or following an optional (but preferred) intervening oxidative bleaching treatment thereof.

As a general rule, the multistep treatment involving the indicated carbon adsorbent decolorizing operation is preferably employed in those instances wherein the glycoside feedstock is quite dark in color (e.g., having an extinction coefficient in the range of from about 3 to about 20) and such decolorizing step or operation is typically employed to substantially lighten the color thereof (e.g., to an extinction coefficient in the range of from about 1 to about 6).

In carrying out the indicated carbon adsorbent treatment, it is generally preferred to contact an aqueous solution of the dark colored glycoside product of concern (at a pH of from about 3 to about 7, at ambient or elevated temperature and at a glycoside product content of from about 10 to about 80 weight percent on a total aqueous solution weight basis) with from about 0.1 to about 35 weight percent (on an aqueous glycoside solution weight basis) of a porous, particulate carbon adsorbent for a time sufficient (typically from about ½ to about 24 hours) to measurably improve the color said aqueous glycoside solution and thereafter separating said carbon adsorbent from the aqueous glycoside solution.

In practicing the above-described carbon treatment step, the carbon adsorbent is preferably employed in powdered form and the amount of powdered carbon adsorbent utilized is preferably from about 0.5 to about 10 (especially from about 1 to about 5) weight percent on an aqueous glycoside solution weight basis. It is also generally preferred (a) that the aqueous glycoside solution contain from about 20 to about 80 (more preferably from about 40 to about 75 and most preferably from about 45 to about 75) weight percent of glycoside product solids dissolved therein on a total glycoside solution weight basis when said solution is subjected to the indicated carbon treatment; (b) that the carbon treatment temperature be from about 20° to about 150° C. (more preferably from about 40° to about 120° C. and most preferably from about 60° to about 100° C.); (c) that the treatment pH be from about 3.5 to about 5.5; and (d) that the treatment time be from about ½ to about 12 (most preferably from about ½ to 2) hours.

As has also been noted above, another preferred embodiment of the present invention involves a multistep process wherein a darker than is ultimately desired glycoside product of interest is subjected to an oxidative bleaching operation to substantially lighten the color thereof prior to the above-described borohydride treatment hereof. As a general rule, the indicated oxidative bleaching step is most beneficially employed in connection with glycoside feedstocks entering the bleaching process with extinction coefficients in the range of from about 0.5 to about 6 and is suitably used to reduce the extinction coefficients of such feedstocks to a value in the range of from about 0.1 to about 0.5. Accordingly, in those instances wherein the glycoside feedstock available for use has an extinction coefficient of about 2 to about 6 or more, it is generally preferred to decolorize said feedstock pursuant to the above-described carbon adsorbent treatment prior to subjecting same to the oxidative bleaching treatment hereof.

Oxidative bleaching agents suitable for use herin include oxygen, ozone, hydrogen peroxide, hypochlorite salts, chlorine dioxide, percarbonates, persulfates, perborates, peracetates, etc. (preferably hydrogen peroxide and hypochlorite salts such as sodium hypochlorite, lithium hypochlorite, calcium hypochlorite, potassium hypochlorite, etc.) and such oxidative bleaching agents are typically employed in an amount ranging from about 0.1 to about 5 (preferably from about 0.05 to about 1.5 and most preferably from about 0.05 to about 0.75) weight percent on a glycoside product dry weight basis.

The indicated oxidative bleaching step is typically conducted with the glycoside product being in the form of an aqueous solution (glycoside product content preferably being from about 20 to about 80 weight percent on a total solution weight basis) and at a temperature of from about 20° to about 90° C., at a pH of from about 4 to about 11; and over a time period of from about 0.5 to about 12 hours. It is also generally preferred that the oxidative bleaching agent employed be added incrementally during the course of the indicated bleaching step.

In those instances wherein a hypochlorite salt is employed as the oxidative bleaching agent, it is generally most preferred to conduct the bleaching step at a temperature in the range of from about 20° to about 45° C. and at a pH in the range of from about 6 to about 11.

In those instances wherein hydrogen peroxide is employed as the oxidative bleaching agent, it is generally most preferred to conduct the bleaching step at a temperature in the range of from about 45° to about 90° C. and at a pH of from about 5 to about 10.

The treated glycoside products resulting from the practice of the present invention are substantially improved in terms of their resistance to color degradation (i.e., discoloration or darkening) upon prolonged storage at ambient or elevated temperatures or to highly alkaline aqueous environments. As a result, said products are more readily acceptable for use in various end-use applications (e.g., as chemical intermediates, in condensation polymerization applications, in alkaline detergent formulations, etc.) involving one or both of the indicated conditions.

In preferred instances, glycoside products treated in accordance with the present invention have an extinction coefficient which is (a) about 0.25 or less when determined at a pH of about 7 as initially prepared; (b) about 0.3 or less when determined at a pH of about 11 as initially prepared; and (c) about 0.5 or less after exposure, at a pH of about 11, to a temperature of about 100° C. for a time period of about 1 hour.

The present invention is hereinafter further described and illustrated by the following examples thereof in which all parts and percentages are on a weight basis unless otherwise indicated.

EXAMPLE 1

In this example an aqueous solution containing, on a total aqueous solution weight basis, about 55 weight percent of a $C_{12-13}$ alkyl glucoside surfactant having an average degree of polymerization of about 1.8 is bleached with sodium hypochlorite (in an amount sufficient to provide 0.46 weight percent active chlorine on a alkyl glucoside dry weight basis) for 8 hours at room temperature (i.e., 20°-25° C.) and at a pH of about 7 to about 10. The resulting bleached product is then treated, at an ambient temperature of about 23° C. and a pH of about 11 to 12.5 for the time period indicated below, with 0.46 weight percent of sodium borohydride (alkyl glucoside dry weight basis).

The extinction coefficient of the indicated alkyl glucoside solution at various stages of the treatment process and following heat stress testing at 100° C. and pH=11 to 12.5 for 1 hour is determined to be as follows:

| TREATMENT STAGE OR STORAGE CONDITIONS | EXTINCTION COEFFICIENT |
| --- | --- |
| Prior to bleaching | 3.18 |
| Treatment for 3 days at room temp. | 0.46 |
| Treatment for 3 days at room temp. followed by heating at 100° C. for 1 hour | 0.52 |
| Treatment for 8 days at room temp. | 0.34 |
| Treatment for 8 days at room temp. followed by heating at 100° C. for 1 hour | 0.50 |
| Treatment 25 days at room temp. | 0.19 |

By comparison, the glucoside surfactant solution when subjected to the bleaching treatment only and not followed by the borohydride treatment becomes as dark as or darker than the original unbleached starting material when stored under the same pH and temperature conditions in the absence of the borohydride material.

EXAMPLE 2

In this example, an aqueous $C_{12-13}$ alkyl glucoside surfactant solution (55 weight percent alkyl glucoside on a total solution weight basis) similar to that of Example 1 is treated with a powdered carbon adsorbent (5 weight percent carbon based alkyl glucoside solids) at a temperature of about 85° C. and a pH of about 5.4 for a time period of about 8 hours; bleached with sodium hypochlorite (0.23 weight percent active chlorine on an alkyl glucoside weight basis (time=8 hours, temperature=23° C. and at a pH of from about 7 to about 10) following carbon adsorbent removal; and then treated with 0.23 weight percent sodium borohydride (alkyl glucoside weight basis) at a pH of from about 11 to 12.5 at room temperature for the time period indicated below.

The extinction coefficient of the indicated alkyl glucoside solution at various stages of the overall treatment process and following heat stress testing at 100° C. and pH=11 to 12.5 for 1 hour is observed to be as follows:

| TREATMENT STAGE OR STORAGE CONDITIONS | EXTINCTION COEFFICIENT |
| --- | --- |
| Prior to carbon treatment | 3.18 |
| Following carbon treatment | 1.32 |
| Treatment for 3 days day at room temp. | 0.33 |
| Treatment for 3 days at room temp. followed by heating for 1 hour at 100° C. | 0.45 |
| After NaBH$_4$ treatment for 8 days at room temp | 0.25 |
| Treatment for 8 days at room temperature followed by heating for 1 hour at pH = 11-12, 100° C. | 0.45 |
| Treatment for 25 days at room temp. | 0.20 |

By comparison, the bleached surfactant solution (i.e., without borohydride treatment) becomes as dark as or darker than the carbon treated starting material upon storage under the same pH and temperature conditions in the absence of the borohydride material.

EXAMPLE 3

In this example an aqueous solution containing, on a total aqueous solution weight basis, about 55 weight percent of a $C_{12-13}$ alkyl glucoside surfactant having an average degree of polymerization of about 1.3 is bleached with sodium hypochlorite (in an amount sufficient to provide 0.45 weight percent active chlorine on a alkyl glucoside dry weight basis) for 8 hours at room temperature (i.e., 20°-25°C.) and at a pH of about 7 to 10. The resulting bleached product is then treated, at 38° C. and a pH of 11.7, with 0.2 weight percent of sodium borohydride (alkyl glucoside dry weight basis).

The extinction coefficient of the indicated alkyl glucoside solution at various stages of the treatment process is determined to be as follows:

| TREATMENT STAGE | EXTINCTION COEFFICIENT |
| --- | --- |
| Prior to bleaching | 2.6 |
| After bleaching | 0.18 |
| NaBH$_4$ treatment for 18 hours at pH = 11.7 | 0.27 |
| NaBH$_4$ treatment for 24 hours at pH = 11.2 | 0.25 |
| Following quenching to about pH = 8 subsequent to the 24 hour NaBH$_4$ treatment | 0.22 |

The treated glycoside product (i.e., following 24 hour NaBH$_4$ treatment and quenching to a pH about 8) is found to be relatively resistant to discoloration upon exposure to elevated temperature/pH conditions (i.e., the extinction coefficient thereof not increasing to more than 0.5 upon heating for 1 hour at 100° C. and at a pH of about 11-12). In contrast, a corresponding bleached glucoside surfactant sample not subjected to the borohydride treatment is found to darken to an extinction coefficient similar to that of the unbleached starting material when subjected to the same elevated temperature/pH conditions.

EXAMPLE 4

In this example, an aqueous $C_{12-13}$ alkyl glucoside surfactant solution (55 weight percent alkyl glucoside on a total solution weight basis) similar to that of Example 1 is treated with a powdered carbon adsorbent (1 weight percent carbon based on alkyl glucoside solids) at a temperature of about 85° C. and a pH of about 5.4 for a time period of about 8 hours. The carbon adsorbent is then removed by filtration and the resulting filtrate is bleached with sodium hypochlorite (0.75 weight percent active chlorine on an alkyl glucoside weight basis, time=2 hours, temperature=25° C. and pH=about 7 to about 10). The bleached glucoside surfactant solution is then treated with 0.2 weight percent sodium borohydride (alkyl glucoside weight basis) for 3 days at room temperature.

The extinction coefficient of the indicated alkyl glucoside solution at various stages of the overall treatment process and upon storage under different conditions following such treatment is observed to be as follows:

| TREATMENT STAGE OR STORAGE CONDITIONS | EXTINCTION COEFFICIENT |
|---|---|
| Prior to carbon treatment | 3.26 |
| Following carbon treatment | 1.5 |
| After bleaching | 0.23 |
| NaBH$_4$ treatment at room temperature for 3 days | 0.2 |
| Quenched for 2 hours at 70° C. following the indicated 3 day NaBH$_4$ treatment | 0.19 |
| Heat stressed for 1 hour at 100° C. and pH = 11-12 following the 3 day NaBH$_4$ treatment | 0.28 |

In the absence of the indicated borohydride treatment, the bleached glucoside surfactant solution will revert to an extinction coefficient of about 1.5 or greater upon heating for 1 hour at 100° C. and pH=11-12.

When the same glucoside solution is bleached and borohydride treated under the same conditions without prior carbon adsorption, the extinction coefficients after bleaching, 3-day NaBH$_4$ treatment and a 100° C. heat stress test are 0.54, 0.49 and 0.65, respectively.

While the present invention has been described and illustrated by reference to particular embodiments and examples thereof, such is not to be understood as in any way limiting the scope of the instantly claimed invention.

What is claimed is:

1. A method for improving the color stability of glycoside products comprising: treating said glycoside product by contacting the glycoside product with a color stabilizing amount of from about 0.01 to about 2 weight percent, on a glycoside product dry weight basis, of a borohydride material selected from the group consisting of Group I or Group II metal borohydride salts for a time period sufficient to substantially reduce the propensity of said glycoside product to darken upon exposure to elevated temperatures under alkaline conditions.

2. The method of claim 1 wherein the borohydride treatment is conducted by intimately admixing said borohydride material into an aqueous solution of said glycoside product.

3. The metod of claim 2 wherein the aqueous glycoside solution contains from about 10 to about 90 weight percent of said glycoside product on a total solution weight basis.

4. The method of claim 3 wherein the borohydride treatment is conducted at a temperature in the range of from about 20° to about 75° C.

5. The method of claim 4 wherein the borohydride treatment is conducted at a pH of about 8 or above.

6. The method of claim 5 wherein the borohydride treatment is conducted over a time period of from about 1 to about 100 hours.

7. The method of claim 6 wherein the borohydride treatment is terminated by reducing the pH of the aqueous glycoside solution to a value of less than 8.

8. The method of claim 2 wherein from about 0.5 to about 20 weight percent, on an aqueous glycoside solution weight basis, of ethanol is added to the aqueous glycoside solution during or following the borohydride treatment.

9. The method of claim 2 wherein the aqueous glycoside solution is subjected to an oxidative bleaching operation prior to the borohydride treatment by contacting same with from about 0.05 to about 1.5 weight percent, on a glycoside product dry weight basis, of an oxidative bleaching agent selected from the group consisting of oxygen, ozone, hydrogen peroxide, hypochlorite salts, chlorine dioxide, percarbonates, persulfates, perborates and peracetates.

10. The method of claim 2 wherein the aqueous glycoside solution is decolorized by contacting same with a porous, particulate carbon adsorbent prior to the borohydride treatment.

11. The method of claim 9 wherein the aqueous glycoside solution is decolorized by contacting same with a porous, particulate carbon adsorbent prior to the oxidative bleaching operation.

12. The method of claim 1 wherein the borohydride material is an alkali metal borohydride.

13. The method of claim 1 wherein the glycoside product is a glycoside surfactant.

14. The method of claim 13 wherein the glycoside surfactant corresponds to the formula:

$$RO(R'O)_y(Z)_x \qquad (A)$$

wherein R is a monovalent organic radical containing from about 6 to about 30 carbon atoms; R' is a divalent hydrocarbon radical containing from 2 to about 4 carbon atoms; y is a number having an average value of from 0 to about 12; Z represents a moiety derived from a reducing saccharide containing 5 or 6 carbon atoms; and x is a number having an average value from 1 to about 6.

15. The method of claim 14 wherein, in the glycoside surfactant of the formula A, R is an alkyl or alkenyl group containing from about 8 to about 16 carbon atoms; y is zero; and x has an average value of from 1 to about 3.

16. The method of claim 1 wherein the treated glycoside product has an extinction coefficient which is (a) about 0.25 or less as initially prepared when determined at a pH of about 7; (b) about 0.3 or less when determined at a pH of about 11 as initially prepared; and (c) about 0.5 or less after exposure, at a pH of about 11, to a temperature of about 100° C. for a time period of about 1 hour.

17. The method of claim 1 wherein the borohydride treatment is conducted by contacting said borohydride material with a non-aqueous solution of said glycoside product.

* * * * *